(12) United States Patent
Li (10) Patent No.: US 9,089,619 B2
(45) Date of Patent: Jul. 28, 2015

(54) HYBRID NANOCRYSTALS FOR TREATMENT AND BIOIMAGING OF DISEASE

(75) Inventor: Tonglei Li, Lexington, KY (US)

(73) Assignee: University of Kentucky, Lexington, KY (US)

( * ) Notice: Subject to any disclaimer, the term of this patent is extended or adjusted under 35 U.S.C. 154(b) by 2568 days.

(21) Appl. No.: 11/447,037

(22) Filed: Jun. 6, 2006

(65) Prior Publication Data

US 2006/0280680 A1    Dec. 14, 2006

Related U.S. Application Data

(60) Provisional application No. 60/687,438, filed on Jun. 6, 2005.

(51) Int. Cl.
*A61K 9/14* (2006.01)
*A61K 51/00* (2006.01)
*A61M 36/14* (2006.01)
*A61K 51/12* (2006.01)

(52) U.S. Cl.
CPC .............. *A61K 51/1255* (2013.01); *A61K 9/145* (2013.01); *A61K 9/146* (2013.01)

(58) Field of Classification Search
CPC ... A61K 9/145; A61K 9/146; A61K 51/1251; A61K 51/1255; A61K 51/1241
USPC ..................... 424/1.29, 1.33, 1.37, 1.65, 489; 977/707, 715, 788, 790, 805, 808
See application file for complete search history.

(56) References Cited

U.S. PATENT DOCUMENTS 6,689,338 B2 * 2/2004 Kotov ........................... 424/1.69
2008/0279949 A1 * 11/2008 Merisko-Liversidge et al. .............................. 424/489

OTHER PUBLICATIONS

Kohler, N. et al., J. Am. Chem. Soc., 2004, 126, p. 7206-7211.*
Sun, S. et al., J. Am. Chem. Soc., 2002, 124, p. 8204-8205.*
Muller, R. et al., J. Biotechnol., 2004, 113, p. 151-170.*
Gekle, M. et al., Am J Physiol Renal Physiol 268: F899-F906, 1995.*
Stella, B. et al., J. Pharm. Sci., 2000, 89(11), p. 1452-1464.*
Sekhon, B., ARS Pharmaceuticals, 2009, 50(3), p. 99-117.*
Trask, A., Molecular Pharmaceutics, 2007, 4(3), p. 301-309.*
Childs, G. "Receptor Mediated Endocytosis," Aug. 10, 2001, http://www.cytochemistry.net/Cell-biology/recend.htm.*
Ford, Am J. Physiol., 1994, 266, p. C52-7, (abstract).*
Carlsson, et al., "Tumour therapy with radionuclides: assessment of progress and problems" Radiotherapy and Oncology 66, 2003, pp. 107-117, Department of Oncology, Radiology, and Clinical Oncology et al., Uppsala, Sweden.
Lu, et al., "Folate-mediated delivery of macromolecular anticancer therapeutic agents" Advanced Drug Delivery Reviews 54, Apr. 18, 2002, pp. 675-693, Department of Chemistry, West Lafayette, Indiana, USA.
Barth, "A critical assessment of boron neutron capture therapy: an overview" Journal of Neuro-Oncology 62, 2003, pp. 1-5, Department of Pathology, The Ohio State University, Columbus, Ohio, USA.
Kahr, et al., "Dyeing Crystals" Chemical Rev. 2001, American Chemical Society, 2001, pp. 893-951, Department of Chemistry, University of Washington, Seattle Washington, USA.
Antonietti, et al., "Nonclassical Shapes of Noble-Metal Colloids by Synthesis in Microgel Nanoreactors" Angewandte Chem. Int. Engl., 1997, pp. 2080-2083, vol. 36, No. 19.

* cited by examiner

*Primary Examiner* — Michael G Hartley
*Assistant Examiner* — Leah Schlientz
(74) *Attorney, Agent, or Firm* — Crowell & Moring LLP (57) ABSTRACT

Hybrid nanocrystals able to reach specific targets in the body for treatment and biological imaging are provided, as well as methods of making and administering same for treatment of disease conditions and for bioimaging and radiotherapy. The hybrid nanocrystals and methods can be used alone or in combination with other treatment and imaging modalities.

20 Claims, 6 Drawing Sheets

HYBRID NANOCRYSTALS FOR TREATMENT AND BIOIMAGING OF DISEASE

FIELD OF THE INVENTION

Hybrid nanocrystals able to reach specific targets in the body for treatment and biological imaging are provided, as well as methods of making and administering same for treatment of disease conditions and for bioimaging. The hybrid nanocrystals and methods can be used alone or in combination with other treatment and imaging modalities.

BACKGROUND OF THE INVENTION

The current doctrine of drug delivery requires the solubilization of the drug substance before delivery can occur. In the treatment of disease, the efficacy of many drugs is limited by poor solubility and severe side effects. After decades of research in drug delivery, almost all possible solubilization methods have already been identified. Targeted delivery, i.e., chemically linking a ligand to the delivery vehicle in order to spare normal cells and to kill targeted cells, such as cancer cells and tumors, has been tested. Despite these efforts, it is still very difficult to deliver drugs to specifically targeted sites.

The synthesis of ligand-conjugated systems can be difficult. It is even more difficult to achieve targeted drug delivery, while maintaining the solubility of insoluble drugs. One common strategy is to conjugate ligand molecules, which bind to specific receptors on the target cell surface, into the drug delivery system. This often requires the chemical linkage between a ligand and the polymer carrier that encapsulates the anticancer drug. One of the few such systems is based on liposomes, or micelles. However, these bioconjugates polymeric systems are complex and challenging to synthesize. Moreover, it is often difficult to maintain the integrity of the delicate delivery system during storage. Delivery systems are delicate and fragile, particularly during systemic circulation. In addition, every delivery vehicle works on its own, surrounded and solvated by the solvent (i.e., water). As a result, the amount of drug which eventually reaches each targeted cell may be considerably limited. For targeted delivery of bioimaging and radiotherapy agents, it is even more critical for the collective emission of radiation by a cluster of radioisotopes to occur. However, current delivery platforms do not satisfy these requirements.

Thus, there is a need for a delivery system which can target specific disease and/or imaging sites, while still avoiding the problems associated with lack of solubility and efficacy associated with current drug delivery models.

SUMMARY OF THE INVENTION

The invention provides for new methods, hybrid nanocrystals, and combination therapies for treating disease and/or for use in biological imaging. The hybrid nanocrystals, methods, compositions and combination therapies are preferably directed towards the treatment of diseases most effectively treated through cell targeting, such as cancers, though any disease condition may be treated.

Accordingly, one aspect of the invention provides for a hybrid nanocrystal, comprising a drug providing a crystal lattice, and a ligand, wherein the ligand induces receptor-mediated endocytosis when released from the hybrid nanocrystal or presented on the crystal surface. The ligand may be stoichiometrically integrated forming co-crystals, or may be entrapped as defects. The drug may be a chemotherapeutic drug. The chemotherapeutic drug may be selected form the group consisting of paclitaxel, camptothecin, and doxorubicin, or other poorly soluble drugs. The hybrid nanocrystal further comprises biocompatible polymers, such as poly(ethylene glycol) and/or further comprises a radionucleotide. The radionucleotide may be I-123, I-131, Sm-153, Tc-99, In-111, Ga-67, F-18, C-11, and/or O-15. Neutron capture agents, such as boron, may be integrated as well.

Preferably, the ligand allows targeting of the hybrid nanocrystals to specific cells in a subject. The hybrid nanocrystals may further comprise antibodies.

Also provided is a method of preparing the hybrid nanocrystals, comprising preparing crystals of the drug in the presence of the ligand, radioisotopes, and/or polymers.

Further provided is a method for treating a disease comprising administering the hybrid nanocrystals to a subject in need thereof in an amount sufficient to treat or inhibit the disease. The disease may be a malignancy. The malignancy may be a tumor, a melanoma, a breast cancer, a prostate cancer, a leukemia, a lymphoma, or other type of solid tumor.

The subject may be further treated with one or more chemotherapeutic agents and/or radiotherapy. The hybrid nanocrystals are preferably administered intravenously, orally, nasally, pulmonary, or intramuscularly. The hybrid nanocrystals may be administered daily, weekly, or monthly.

The present invention also provides a method of biological imaging, comprising administering the hybrid nanocrystals comprising a radionucleotide.

Also provided is a combination therapy for inhibiting tumor growth and/or metastatic progression and/or development of metastases comprising administering the hybrid nanocrystals, an immunotherapeutic, and/or radiation therapy.

BRIEF DESCRIPTION OF DRAWINGS

FIG. 3 shows photographs of the hybrid nanocrystals. 3A shows acetaminophen with fluorescin, 3B shows aspirin with fluorescin, and 3C shows aspirin with methylene blue.

DETAILED DESCRIPTION OF THE INVENTION

Figure 1:
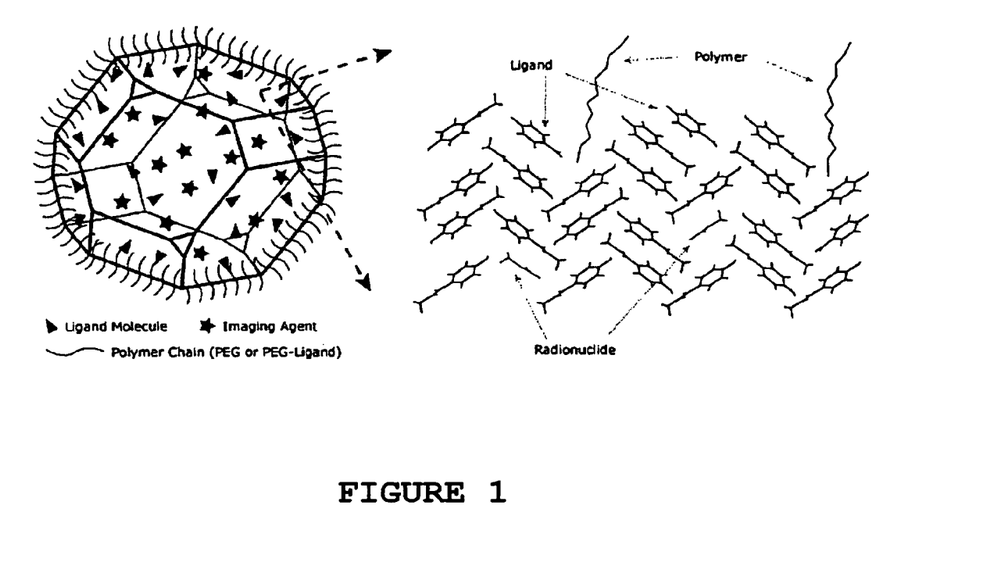
FIG. 1 shows the hybrid nanocrystals with integrated functional molecules and/or atoms such as radioisotopes, antibodies, and ligands into the crystal matrix of the therapeutic material.
Figure 2:
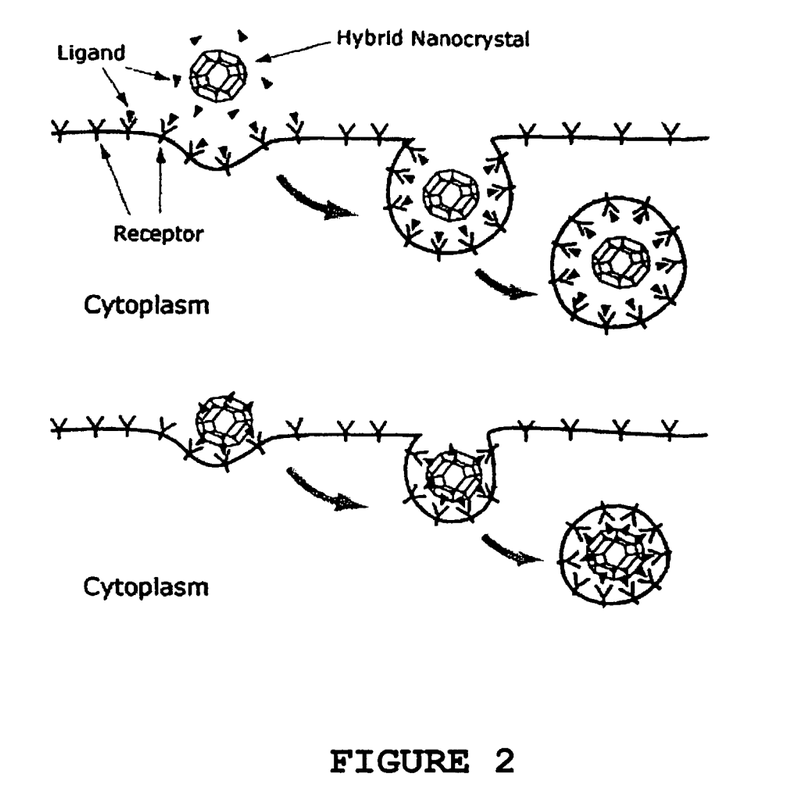
FIG. 2 shows receptor-mediated endocytosis (RME). Ligand molecules are released when hybrid nanocrystals dissolve induce RME. Anything within the vicinity of a ligand-receptor binding site, including the hybrid nanocrystals, can be internalized by the cells. Alternatively or concurrently, ligands fixated on the crystal surface will cause RME. Even as the hybrid nanocrystals are dissolving, there are still fresh ligands on the crystal surface.
Figure 3:
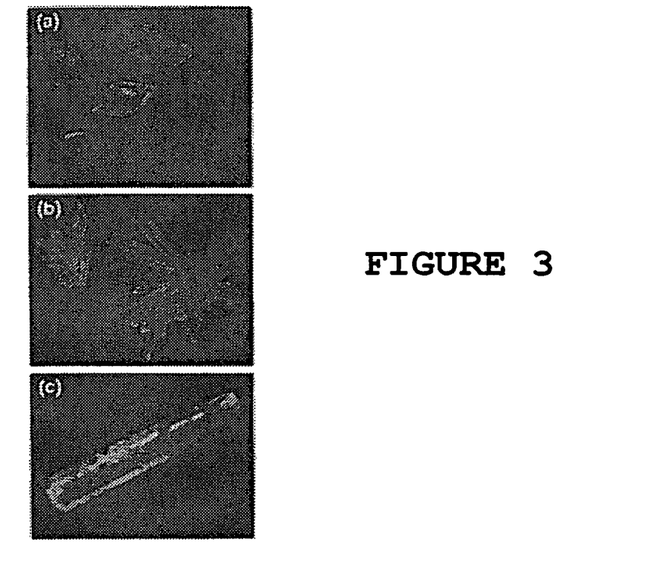
Figure 4:
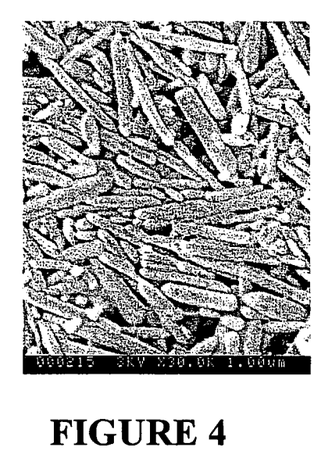
FIG. 4 shows hybrid nanocrystals of indomethacin and folic acid. The average size was about 800 nanometers.
Figure 5:
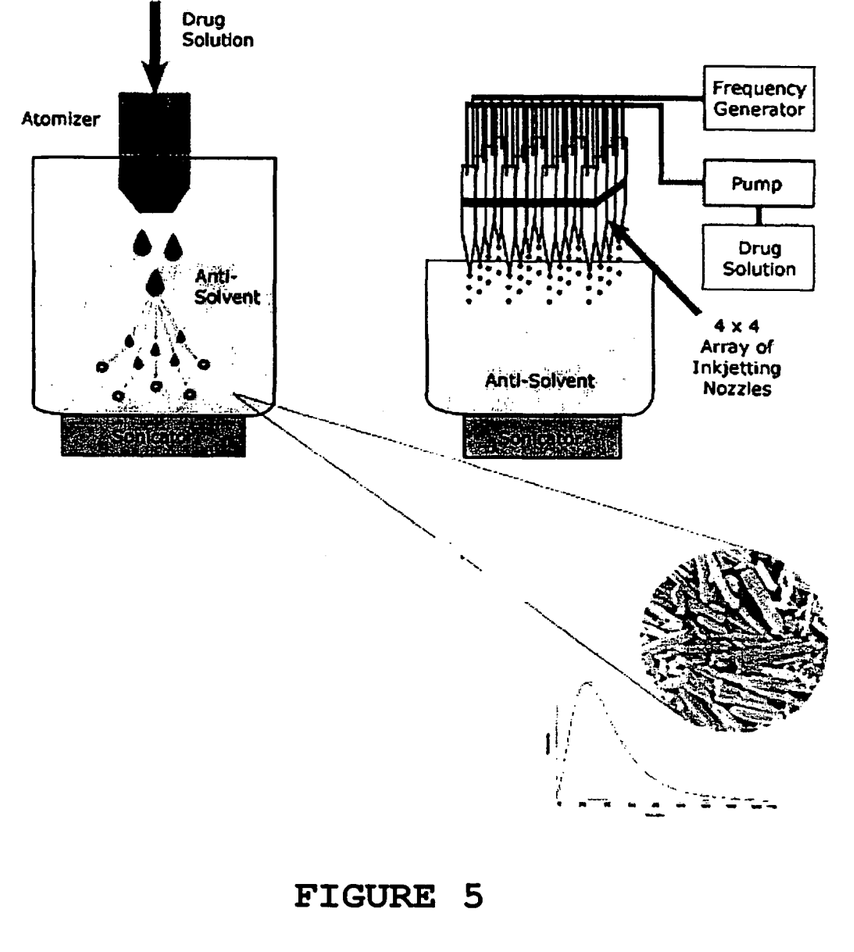
FIG. 5 illustrates the making of hybrid nanocrystals. The hybrid nanocrystals may be prepared by atomizing the drug solution, followed by exposing the droplets to the anti-solvent. The experimental setups shown are proposed for the growth of hybrid nanocrystals. Using a large array of inkjetting nozzles will achieve better control of particle size and distribution, with a high yield.
Figure 6:
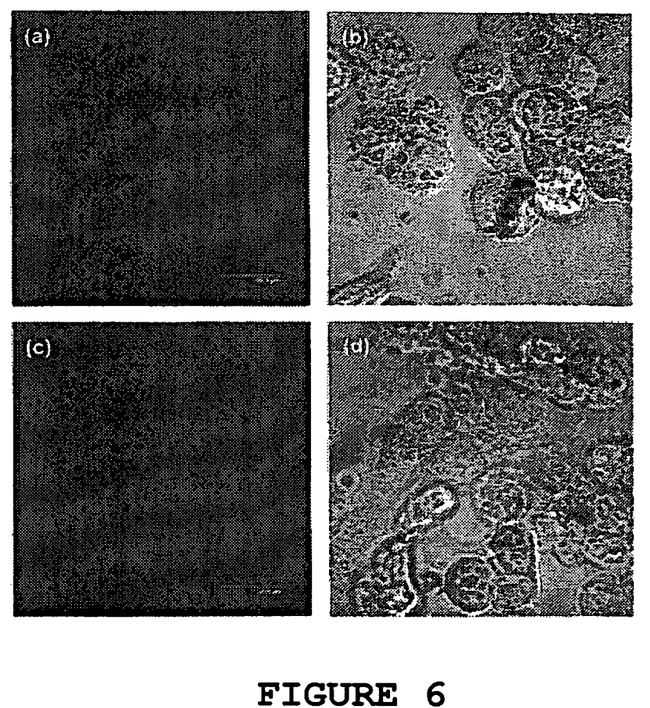
FIG. 6 shows photos from in vitro tests. Confocal images of KB cells incubated with indomethacin nanocrystals (5A and 5B) and KB cells incubated with indomethacin-ligand hybrid nanocrystals (5C and 5D) are shown. The difference in cellular uptake between a drug nanocrystal and drug-ligand hybrid nanocrystal is illustrated. Fluorescence of hybrid crystals was much stronger than that of drug crystals alone, indicating a strong specificity by the hybrid crystals to the cells. The punctate image (5C) furthers suggests that the hybrid crystals were enclosed by the cell endosomes.

In accordance with this detailed description, the following abbreviations and definitions apply. It must be noted that as used herein, the singular forms "a", "an", and "the" include plural referents unless the context clearly dictates otherwise. Thus, for example, reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

DEFINITIONS

By the term "subject" or "patient" as used herein is meant to include any animals, preferably a mammal. The mammal can be a canine, feline, primate, bovine, ovine, porcine, camelid, caprine, rodent, or equine. Preferably the mammal is human.

The term "efficacy" as used herein refers to the effectiveness of a particular treatment or imaging regime. Efficacy can be measured based on such characteristics (but not limited to these) as inhibition of disease, reduction of tumor mass, slowed disease or tumor growth, lack of detectable disease or tumor associated antigens, and the like. Additional methods of assessing disease progression would be known to the treating and diagnosing physicians.

The terms "treating", and "treatment", and the like are used herein to generally mean obtaining a desired pharmacological and physiological effect. More specifically, the reagents described herein which are used to treat a subject with a disease generally are provided in a therapeutically effective amount to achieve any one or more of the following: inhibited disease progression, reduction in tumor mass, or reduction in disease or tumor such that there is no detectable disease, as assessed by well known methods.

The term "treatment", as used herein, covers any treatment of a disease in any animal, preferably a mammal, particularly a human.

By "therapeutically effective amount" is meant an amount of an agent, reagent, compound, composition, or combination of reagents disclosed herein that when administered to an animal is sufficient to be effective against the disease condition.

By the term "tumor" is meant to include both benign and malignant growths or cancer. Thus, the term "cancer", unless otherwise stated, can include both benign and malignant growths. Preferably, the tumor is malignant. The tumor can be a solid tissue tumor such as a melanoma, or a soft tissue tumor such as a lymphoma, a leukemia, or a bone cancer.

By the terms "metastatic disease", "metastases", and "metastatic lesion" are meant a group of cells.

The present invention provides solid-based, hybrid, nanosized, multifunctional therapeutic and diagnostic systems for direct access to disease sites (for example, a tumor site). Because of ligand-induced receptor-mediated endocytosis (RME), the hybrid nanocrystals can be taken up by targeted cells directly. The present invention provides hybrid nanocrystals where ligands, radioactive elements and/or other elements are integrated in the crystal lattice of a drug. The hybrid nanocrystals do not require solubilization in order to achieve drug delivery, and thus overcome the solubility requirement and side effects associated with current delivery methods for disease therapy. The use of hybrid nanocrystals significantly improves therapeutic, bioimaging, and radiotherapy efficacy.
Hybrid Nanocrystals The hybrid nanocrystals of the present invention contain integrated ligand molecules that make it possible to target drug nanocrystals to cancer tumors due to the specific binding between the ligand the receptor of targeted cells. Ligand molecules exposed on the crystal surface act as a "homing device" for the targeted delivery.

For targeted drug delivery, the traditional method has been to chemically link a ligand to a polymer carrier that encapsulates the drug, leading to typical formulations such as liposomes, micelles, emulsions and polymers, i.e., coated solid nanoparticles. However, these known techniques are fragile, complicated and difficult to scale up. The present invention provides drug hybrid nanocrystals for disease therapy. Nanosized crystals of drugs are provided together with a ligand to physically integrate ligand molecules into the crystal lattice. Instead of delivering drug molecules, the drug hybrid nanocrystals can be introduced into targeted cells. The integrated ligand molecules allow drug nanocrystals to target cells and tumors due to the specific binding between ligand and its receptor on the cell surface. Exposed on crystal, ligand molecules act as a "homing device", binding a nanocrystal to the target cell and triggering receptor-mediated endocytosis for the cellular uptake of whole nanocrystals. Concurrently, ligand molecules that are released when hybrid crystals slowly dissolve will induce receptor-mediated endocytosis. Anything within the vicinity of a ligand-receptor binding site, including nanocrystals, can be internalized by cells. Over time, nanocrystals inside cells release sufficient drug molecules to treat the disease or to result in cell death, depending on the drug utilized.

The incorporation ratio of foreign molecules may be a few hybrid nanocrystal percentage or more. Due to the physical strength of a crystal structure, the integration of ligand molecules is strong enough to bring a hybrid nanocrystal into a cell through the endocytosis. Even as a crystal keeps dissolving, freshly exposed surfaces still have ligand molecules available. The hybrid nanocrystals of the present invention can be applied to delivering bioimaging agents, radionuclides, and neutron capture chemicals.

For the drug providing the crystal lattice of the hybrid nanocrystals, any drug may be used and delivered into the body. Preferably, the drug is one which has increased the treatment efficacy in the body if targeted to specific cells. With regard to forming hybrid nanocrystals, poorly soluble drugs may be preferred due to their strong intermolecular interactions in crystal. For example, chemotherapeutic drugs such as paclitaxel, camptothecin, and doxorubicin as crystal hosts are preferred, as they can be readily targeted to cancer cells, using the hybrid nanocrystals of the present invention. Any ligand may be used, as appropriate. For example, folic acid may be used as a ligand. The hybrid nanocrystal may further comprise polymers, such as poly(ethylene glycol) and/or radionucleotide. The radionucleotide may include, but is not limited to, I-123, I-131, Sm-153, Tc-99, In-111, Ga-67, F-18, C-11, and/or O-15. Neutron capture agents, such as boron, may also be included.
Methods of Preparing Hybrid Nanocrystals The hybrid nanocrystals of the present invention are grown from "the bottom up", with the crystal lattice of the drug growing in the presence of the ligands and other desired elements. Thus, once the crystal is complete, all desired elements are already incorporated into the crystal. This method is an improvement over known methods of crystal preparation which break down crystals.

Techniques to grow nanocrystals include spraying drying, using anti-solvent, and crystallization in microemulsions. It has been demonstrated regularly to grow guest molecules, such as dyes, into molecular crystals. Thus, it is technically feasible to grow nanocrystals of a drug with an integrated ligand.

Hybrid nanocrystals may be developed through antisolvent, supercritical carbon dioxide, spray drying, and/or salting out methods. To control the size of crystals, frequency-modulated atomizers are used in order to produce liquid droplets smaller than 6 µm. Solvents and additives are critical for controlling the size of the crystals, as well as the concentration and distribution of functional molecules in the hosting crystal. Quantum mechanical calculations may be used to select proper crystallization conditions. The resulting crystals may be about 200-500 nanometers in size.

A ligand, such as folic acid, may be dissolved in a selected solvent, such as a basic aqueous solution. PVP, Tween 80®, or poly(ethylene glycol) may be added to the solution and then diluted with distilled water. The drug may be dissolved into a solvent, such as ethanol. Under sonication, the drug solution is atomized and injected into the ligand solution. Alternatively, the drug and ligand may be dissolved in an effective solvent, and atomized and injected into an anti-solvent. The final solution is stirred and then centrifuged to remove supernatant. Sonication is repeated with fresh water to resuspend the nanocrystals. This procedure may be repeated to remove any surfactants, polymers, and/or loosely bound ligands.

Testing the Efficacy of Targeting and Cell Toxicity

Cell studies may be carried out with ligand deficient cells (e.g., HL-60) and breast cancer cells (e.g., MCF-7) for determining targeting effectiveness and cell viability. An athymic mouse model may be used for the in vivo tests of both bioimaging and therapeutic efficacy. Cultured tumor cells may be introduced to mice and allowed to grow to a certain size. Hybrid nanocrystals may be administered and the distribution of the crystals in different organs and the cancerous mass will be determined.

Treatment

In one aspect of the invention, the hybrid nanocrystals and methods may be used to diagnose, inhibit, treat, and/or slow progression of disease. Many treatments exist for disease states. The particular therapy or combination of therapy modalities used depend greatly on the type of disease, its stage, the patient (e.g., weight, sex, age, health, prior cancers, and the like), and where the patient is in therapy. Therefore, physicians will frequently have to combine a variety of treatment modalities that will best suit the needs of the patient in combating the disease and the patient's self-determination of quality of life. Treatment modalities include but are not limited to surgery, radiation therapy, chemotherapy, biologic therapy (e.g., cytokines, immunotherapy, and interferons), hormone therapies, and hyperthermia.

In the instance of cancer treatment, chemotherapy can be further broken down into hormone therapies (e.g., antiestrogens, aromatase inhibitors, gonadotropin-releasing hormone analogues, and anti-androgens), anti-tumor alkylating agents (e.g., mustards, nitrosoureas, tetrazines, and aziridines), cisplatin and its analogues, anti-metabolites (e.g., methotrexate, antifolates, 5-fluoropyrimidines, cytarabine, azacitidine, gemcitabine, 6-thipurines, and hydroxyurea), topoisomerase interactive agents, antimicrotubule agents (e.g., vinca alkaloids, taxanes, and estramustine), differentiating agents (e.g., retinoids, vitamin D3, polar-apolar compounds, butyrate and phenylactetate, cytotoxic drugs, cytokines, and combinations thereof), and other chemotherapeutic agents such as fludarabine, 2-chlorodeoxyadenosine, 2'-deoxycoformycin, homoharringtonine (HHT), suramin, bleomycin, and L-asparaginase.

The present invention contemplates the use hybrid nanocrystals for the treatment of disease by administration to a subject in need. The hybrid nanocrystals may be administered in a variety of ways including but not limited to parenteral administration, including subcutaneous (s.c.), subdural, intravenous (i.v.), intramuscular (i.m.), intrathecal, intraperitoneal (i.p.), intracerebral, intraarterial, or intralesional routes of administration, localized (e.g., surgical application or surgical suppository), and pulmonary (e.g., aerosols, inhalation, or powder). Preferably, the hybrid nanocrystals are administered intravenously or parenterally.

The hybrid nanocrystals may be put into water and then directly administered. The hybrid nanocrystals do not need to be solubilized, but rather suspended in the water. The dose administered will be determined by route of administration, as well as other factors well known to physicians such as patient weight and disease. Preferred routes of administration include parenteral, subcutaneous, or intravenous administration.

For parenteral administration, the hybrid nanocrystals of the invention can be administered as injectable dosages. A polymer or other agent for effecting solubility is not required. Administration of other therapeutic agents can occur prior to, concurrent with, or after administration with the immunoglobulin. Administration of the subject hybrid nanocrystals can occur before, during or after surgical treatment, or other therapy. Administration of the subject hybrid nanocrystals can occur daily, weekly, or monthly as needed.

A typical daily dosage might range for hybrid nanocrystals from about 1 µg/kg to up to about 200 mg/kg subject weight or more, more preferably from about 0.01 mg/kg to about 150 mg/kg subject weight, more preferably from about 0.1 mg/kg to about 100 mg/kg subject weight, more preferably from about 1 mg/kg to about 75 mg/kg patient weight (and every integer value between these values) depending on the factors mentioned herein. Typically, the clinician will administer hybrid nanocrystals until a dosage is reached that achieves the desired effect. The progress of this therapy can be easily monitored by conventional assays. A "stable" formulation is one in which the protein therein essentially retains its physical stability and/or chemical stability and/or biological activity upon storage. Stability can be measured at a selected temperature for a selected time period.

An active ingredient within the hybrid nanocrystals, providing the crystal lattice of the hybrid nanocrystal, "retains its biological activity", if the biological activity of the hybrid nanocrystals at a given time is within about 10% (within the errors of the assay) of the biological activity exhibited at the time the pharmaceutical formulation was prepared.

Because nanocrystals are solid, consumption of the crystals is expected to take time. Thus, if hybrid nanocrystals can accumulate in the tumor site, a local dose may last for days, providing a sustained release property. Thus, a preferred method of administration for treatment of a solid tumor may be direct injection into the solid tumor.

Use of Hybrid Nanocrystals in Biological Imaging and Radiotherapy

The hybrid nanocrystals of the present invention may be used in biological imaging. The targeting ability of the hybrid nanocrystals can be utilized to locate and image specific areas of the body, such as tumors.

Increasing the dose or amount of radioisotopes that are integrated in the hybrid nanocrystals may be used for radiotherapy. The radiation emitted from the nanocrystals that are targeted to a tumor site may cause apoptosis of cancerous or malignant cells.

Use of Hybrid Nanocrystals for Simultaneous Diagnosis and Treatment

Hybrid nanocrystals may be used to deliver drugs and radioisotopes simultaneously. Radionucleotides and ligands may be integrated in the crystal lattice of the drug agent in order to achieve both diagnosis and treatment.

Although the present invention has been described in detail with reference to examples below, it is understood that various modifications can be made without departing from the spirit of the invention, and would be readily known to the skilled artisan.

EXAMPLES

Example 1

Breast cancer and other cancers are often treated with cytotoxic chemotherapy, with antineoplastic compounds such as paclitaxel. However, two major limitations are associated with these cytotoxic drugs. Both poor water solubility and severe side effects are associated with using these compounds and affect the efficacy of the treatment.

The use of ligand-drug hybrid nanocrystals for the targeted delivery against the breast cancer is explored. Crystals of an anticancer drug are grown together with a ligand in order to trap ligand molecules in the crystal lattice. It is theorized that integrated ligand molecules make it possible to target drug nanocrystals to cancer tumors, due to the specific binding between the ligand the receptor of cancer cells. Ligand molecules exposed on the crystal surface act as a "homing device" for the targeted delivery. Using nanosized crystals allows the direct administration of the dosage (e.g., through intravenous and intramuscular injection) and does not require any solubility in a liquid. Thus, the hybrid nanocrystals avoid the problems of poor solubility of drugs due to the large surface area and possibly direct intake by cells.

The goals of the study are to (1) to grow drug nanocrystals in the presence of a ligand and determine the concentration and distribution of ligand molecules in the drug crystal, and (2) to test the in vitro cytotoxicity (survival rate) difference between normal cells and breast cancer cells with the ligand-drug hybrid nanocrystals.

Paclitaxel and folic acid are used as the model drug and the ligand. Folate receptors are known to be upregulated in many human cancers including breast tumors. In this study, paclitaxel was dissolved into ethanol (which dissolves about 4,000 times more paclitaxel than water). A small amount of folic acid was dissolved in the ethanol as well.

After injecting the solution into water (which serves as the anti-solvent) through an atomizer nozzle, nanocrystals will be formed upon the impact. Additional tests may be done to inject a paclitaxel ethanol solution into a folic acid aqueous solution to produce nanocrystals that may be coated with a layer of drug-ligand or "just ligand" crystals. By re-dissolving the obtained crystals, the concentration of folic acid in the crystals will be determined. To determine the distribution of folic acid in the nanocrystals, a fluorescent molecule will be identified to chemically link to the folic acid. Distribution of the ligand-marker in the crystal may be observed under a fluorescent microscope. Moreover, foliate receptor deficient cells (e.g., HL-60, C6, or GH3) and breast cancer cells (e.g., MCF-7) will be incubated with ligand integrated drug nanocrystals in a 5% $CO_2$ humidifed atmosphere at 37° C. for 12-72 hours. The amount of live cells will be determined by an appropriate method such as the Trypan blue method.

By targeting the folate receptor, this drug delivery system will be developed as a more effective therapeutic approach against breast cancer. The strong, non-chemical integration of the ligand in the drug crystal lattice delivers drug substances into tumor cells with greater specificity. Using hybrid nanocrystals will also make the delivery system very stable and able to achieve longer circulation times.

Example 2

Hybrid nanocrystals will be developed through antisolvent, supercritical carbon dioxide, spray drying, and/or salting out methods. To control the size of crystals, frequency-modulated atomizers will be used in order to produce liquid droplets smaller than 6 μm. Because solvents and additives are critical for controlling the crystals' size as well as the concentration and distribution of functional guest molecules in the hosting crystal, quantum mechanical calculations will be used to select proper crystallization conditions. Paclitaxel, camptothecin, and doxorubicin will be used as crystal hosts, folic acid as the ligand, poly(ethylene glycol) as the biocompatible coating, and iodine-123 as the radionuclide. Other drugs and special agents (such as intracellular targeting agents) may also be tested. Cell studies will be carried out with ligand deficient cells (e.g., HL-60) and breast cancer cells (e.g., MCF-7) for determining targeting effectiveness and cell viability. An athymic mouse model will be used for the in vivo tests of both bioimaging and therapeutic efficacy. Cultured tumor cells will be introduced to mice and will be allowed to grow to a certain size. Hybrid nanocrystals will be administered and the distribution of the crystals in different organs and the cancerous mass will be determined.

This concept overcomes the solubility requirement and side effects associated with current delivery methods for breast cancer therapy. The use of hybrid nanocrystals should significantly improve therapeutic, bioimaging, and radiotherapy efficacy.

Example 3

Development of Hybrid Nanocrystals with Indomethacin 50 mg folic acid was dissolved into NaOH solution. 0.25-0.5 g poly(vinyl pyrrolidone), PVP, was put into solution and then diluted to 50 ml with distilled water. 200 mg of indomethacin was dissolved into 5 ml EtOH. Under sonication (Fisher Model 500 Sonic Dismembrator, Fisher Scientific Inc.) at 40% intensity, the indomethacin solution was added into folic acid solution dropwise. Sonication was continued for 5 minutes. The suspension was stirred magnetically for another 2 hours to stabilize it. Centrifugation at 10000 rpm for 20 minutes was performed to get rid of the supernatant. Sonication was performed again (5 minutes) with fresh water to re-suspend nanocrystals. This procedure was repeated several times to remove extra PVP.

Development of Nanocrystals with Fluoranthene 100 mg fluoranthene was dissolved in 20 ml acetone, and the solution was filtered. Through an ultrasonic atomizer (Type 710.070.16.60, Lechler Inc.), the solution was injected by a syringe pump (KDS-200, KDScientific Inc.) at 0.25 ml/min into a 200 ml water and 0.5 ml Tween 80 solution. The aqueous solution was sonicated by a flat tip homogenizer (Fischer Model 500 Sonic Dismembrator, Fischer Scientific Inc.) at 85% intensity. The sonication was continued after thefluoranthene solution was injected to the water.

Example 4

Delivery of radionucleotides (Carlsson, J.; Aronsson, E. F.; Hietala, S. A.; Stigbrand, T.; Tennvall, J., *Radiotherapy and Oncology* 2003, 66, 107-111) and neutron-capture chemicals to cancer sites Lu, Y. J.; Low, P. S. *Advanced Drug Delivery Reviews* 2002, 54, 675-693) has been widely studied, and used clinically to diagnose and treat the malignancies, including breast cancer. High-energy radiation interrupts the growth of cancer cells, and is one of few successful methods for combating cancer. To reduce side effects and/or enhance the efficacy, the chemicals are often chelated by organic anions (e.g., diethylenetriaminepentaacetic acid) linked covalently by ligand molecules for targeting cancer cells. The conjugated ligands recognize specific receptors over-expressed on cancer cells, inducing receptor-mediated endocytosis for the cellular uptake of chelated radioisotopes. However, ligand-conjugated delivery systems suffer inherited drawbacks that limit their clinical potentials. Because ligand molecules are chemically linked to the delivery system, not only are the synthesis and purification very demanding, but also the integrity of the whole delicate chelation matrix is difficult to maintain particularly during system circulation. More importantly, being dispersed in the aqueous environment, individual chelated complexes may have their radiation significantly "diluted", leading to ineffective radiation synergies, and thus requiring high doses that may pose severe side effects.

The purpose of this study is to test the use solid-state delivery systems for targeting breast cancer. Radioactive or neutron-capture atoms will be "trapped" or integrated inside the crystal lattice of a ligand substance. No chemical synthesis will be needed. Crystals of a ligand will be developed together with a radioactive substance. The process uses incorporation of concentrated guest elements in a hosting solid-state matrix. By forming nanocrystals of the radioisotope-ligand composites, the therapeutic effectiveness will be significantly improved. Radiation therapy may be greatly advanced if strong radiation can be localized and confined in the breast cancer site with fewer side effects. By engineering nanosized hybrid crystals, both targeted delivery and high radiation efficacy can be achieved. Further "hot" or radioactive atoms can be tested, and the concept further evolved by using a chemo agent (such as paclitaxel and camptothecin) as the hosting crystal to integrate ligands and radiochemicals to achieve simultaneous targeting and bioimaging, initiating a new generation of materials to tackle cancers.

The radioactive elements inside a nanocrystal are able to collectively emit a much stronger radiation than that by scattered and solvated radioisotopes. Furthermore, by using a ligand as the crystal host, the targeted delivery can be better assured. The only requirement of the design is that the host crystal needs to be poorly water soluble. This is advantageous, as bioorganic and drug molecules tend to be lipophilic (to cross biomembranes).

Objectives: (1) To grow ligand nanocrystals in the presence of a radioactive or neutron-capture substance, and determine the concentration and distribution of guest elements in the host crystal. (2) To test the in vitro difference in targeting specificity between normal cells and breast cancer cells. The cancer cells over-express receptors which the ligand molecules are able to bind.

Non-radioactive gold (Au) will be used as the model radioisotope and folic acid as the ligand. Au is known to be able to convert to the radioactive 198Au upon radiation. Using a "cold" radioisotope allows for focus on the feasibility study and method development. Folate receptors are known to be upregulated in many human cancers, including breast tumors (Barth, R. F. *Journal of Neuro-Oncology* 2003, 62, 1-5). Folic acid is poorly soluble, about 1.6 µg/ml in water at 25° C. Techniques to grow nanocrystals are mature including spraying drying, salting out, and using anti-solvents. It has been widely demonstrated to grow guest molecules, such as dyes (Kahr, B.; Gurney, R. W. *Chemical Reviews* 2001, 101, 893-951) into hosting organic crystals. In this study, folic acid and $HAuCl_4$ will be dissolved in basic aqueous solution, followed by spaying into natural or acidic aqueous solution of $NaBH_4$ under sonication via a frequency-modulated nozzle. Due to the decrease in solubility of folio acid at lower pH as well as reduction of Au3+ to Au by $NaBH_4$ (Antonietti, M.; Grohn, F.; Hartmann, J.; Bronstein, L. *Angewandte Chemie* 1997, 36, 2080-2083), individual Au atoms or colloids may be integrated and dispersed in the crystals of folic acid. By researching proper experimental conditions, 200-400 nm crystals with 1-10% of gold integrated may be obtained. TEM and elemental analysis will be used to measure the distribution and concentration of Au in the nanocrystals.

Moreover, normal cells (e.g., HL-60, C6, or GH3) and breast cancer cells (e.g., MCF-7) will be incubated with Au-ligand hybrid nanocrystals in a 5% CO2 humidified atmosphere at 37° C. for 12-72 hours. To test the targeting specificity, cellular uptake of nanocrystals will be analyzed by TEM due to high density of Au, and by HPLC for measuring folic acid.

All references cited above are incorporated herein in their entirety for all purposes.

I claim:
1. A hybrid nanocrystal, comprising a drug providing a crystal lattice, and a ligand, wherein the ligand is integrated throughout the nanocrystal as a structural defect, and wherein the ligand induces receptor-mediated endocytosis when released from the hybrid nanocrystal or presented on the crystal surface.
2. The hybrid nanocrystal of claim 1, wherein the drug is a chemotherapeutic drug.
3. The hybrid nanocrystal of claim 1, wherein the drug is poorly soluble.
4. The hybrid nanocrystal of claim 2, wherein the chemotherapeutic drug is selected from the group consisting of paclitaxel, camptothecin, and doxorubicin.
5. The hybrid nanocrystal of claim 1, wherein the hybrid nanocrystal further comprises a radionucleotide, and wherein the radionucleotide is integrated throughout the nanocrystal.
6. The hybrid nanocrystal of claim 1, wherein the hybrid nanocrystal further comprises a biocompatible polymer, and wherein the biocompatible polymer is integrated throughout the nanocrystal.
7. The hybrid nanocrystal of claim 6, wherein the biocompatible polymer is poly (ethylene glycol).
8. The hybrid nanocrystal of claim 5, wherein the radionucleotide is selected from the group consisting of 1-123, 1-131, Sm-153, Tc-99, Ga-67, F-18, C-11, and O-15.

9. The hybrid nanocrystals of claim 1, wherein the ligand allows targeting of the hybrid nanocrystals to specific cells in a subject.

10. The hybrid nanocrystals of claim 1, further comprising antibodies, wherein the antibodies are integrated throughout the nanocrystal.

11. A method of preparing the hybrid nanocrystals of claim 1, comprising preparing crystals of the drug in the presence of the ligand, radioisotopes, and/or polymers.

12. A method for treating a disease comprising administering the hybrid nanocrystals of claim 1 to a subject in need thereof in an amount sufficient to treat or inhibit the disease.

13. The method of claim 12, wherein the disease is a malignancy.

14. The method of claim 13, wherein the malignancy is a tumor is a melanoma, a breast cancer, a prostate cancer, a leukemia, a lymphoma or other solid tumor.

15. The method of claim 12, wherein the subject is further treated with one or more chemotherapeutic agents and/or radiotherapy.

16. The method of claim 12, wherein the hybrid nanocrystals are administered via a route selected from the group consisting of intravenously, orally, nasally, pulmonary, and intramuscularly.

17. The method of claim 12, wherein the hybrid nanocrystals are administered daily, weekly, or monthly.

18. A method of biological imaging, comprising administering the hybrid nanocrystals of claim 5 and performing a biological imaging scan to obtain an image.

19. A combination therapy for inhibiting tumor growth and/or metastatic progression and/or development of metastases comprising administering the hybrid nanocrystals of claim 1, an immunotherapeutic, and/or radiation therapy.

20. A hybrid nanocrystal, comprising indomethacin providing a crystal lattice, folic acid, and poly (vinyl pyrrolidone), wherein the folic acid is integrated throughout the nanocrystal as a structural defect and the poly (vinyl pyrrolidone) is also integrated throughout the nanocrystal.

* * * * *